United States Patent [19]

Gupta et al.

[11] Patent Number: 5,041,382
[45] Date of Patent: Aug. 20, 1991

[54] HIGH CONCENTRATION ENRICHMENT OF CONIFER EMBRYONAL CELLS

[75] Inventors: Pramod K. Gupta, Federal Way; Gerald S. Pullman, Renton, both of Wash.

[73] Assignee: Weyerhaeuser Company, Tacoma, Wash.

[21] Appl. No.: 515,035

[22] Filed: Apr. 26, 1990

Related U.S. Application Data

[63] Continuation-in-part of Ser. No. 321,035, Mar. 9, 1989, Pat. No. 4,957,866.

[51] Int. Cl.$^5$ .................... A01H 4/00; A01H 7/00; C12N 5/04
[52] U.S. Cl. .................... 435/240.45; 435/240.4; 435/240.46; 435/240.47; 435/240.49; 435/240.54; 435/172.1; 800/DIG. 49; 800/DIG. 50; 800/DIG. 51; 800/200
[58] Field of Search ........... 435/240.4, 240.45, 240.46, 435/240.47, 240.49, 240.54, 172.1; 800/DIG. 49

[56] References Cited

U.S. PATENT DOCUMENTS 4,217,730  8/1980  Abo-El-Nil ..................... 47/58

OTHER PUBLICATIONS

Attree, S. M., D. I. Dunstan, and L. C. Fowke 1989 Plantlet Regeneration from Embryogenic Protoplasts of White Spruce (*Pieca glauca*). *Bio/Technology* 7: 1060–1062.

Becwar, M. R., S. R. Wann, and R. Nagmani 1988 A Survey of Initiation Frequency of Embryogenic Callus among Ten Families of *Pinus taeda* (Loblolly Pine). *Abstracts*, 4th International Conifer Tissue Culture Work Group, Aug. 8–12, 1988, Saskatoon, Saskatchewan, Canada.

Bourgkard, F. and J. M. Favre 1988 Somatic Embryos from Callus of *Sequoia sempervirens*, *Plant Cell Reports* 7: 445–448.

Durzan, D. J. and P. K. Gupta 1987 Somatic Embryogenesis and Polyembryogenesis in Douglas-Fir Cell Suspension Cultures. *Plant Science* 52: 229–235.

Gupta, Pramod K. and Don J. Durzan 1986 Somatic Polyembryogenesis from Callus of Mature Sugar Pine Embryos. *Bio/Technology* 4: 643–645.

1987a Biotechnology of Somatic Polyembryogenesis and Plantlet Regeneration in Loblolly Pine. *Bio/Technology* 5: 147–151.

1987b Somatic Embryos from Protoplasts of Loblolly Pine Proembryonal Cells. *Bio/Technology* 5: 710–712.

Hakman, Inger and Sara von Arnold 1985 Plantlet Regeneration through Somatic Embryogenesis in *Picea abies* (Norway Spruce). *Journal of Plant Physiology* 121: 149–158.

Hakman, Inger, L. C. Fowke, Sara von Arnold, and Tage Eriksson 1985 The Development of Somatic Embryos in Tissue Cultures Initiated from Immature Embryos of *Picea Abies* (Norway Spruce). *Plant Science* 38: 33–35.

(List continued on next page.)

*Primary Examiner*—Howard J. Locker
*Assistant Examiner*—Gary Benzion

[57] ABSTRACT

The invention lies in the field of conifer tissue culture. It is especially directed to a method for production of large concentrations of embryonal cells particularly suitable for genetic modification. The cells are enriched in the sense that the ratio of embryonal to nonembryogenic cells is very significantly in crased over that attained by earlier methods. The method comprises first developing an embryonalsuspensor mass containing early stage proembryos from a suitable explant. These are multiplied in a maintenance medium and developed to late stage proembryos in a medium that preferably has an osmotic level raised about 30–50% over the initiation medium. The late stage proembryos are transferred to a new medium that again has the osmotic level raised about 35–55% over the proembryo development medium. After three to six transfers a large number of embryonal cells without suspensors will have formed. These may be used in any of the known methods for genetic alteration.

8 Claims, 4 Drawing Sheets

OTHER PUBLICATIONS

Murashige, Toshio and Folke Skoog 1962 A revised Medium for Rapid Growth and Bioassays with Tobacco Tissue Cultures. *Physiologia Plantarum* 15: 473–493.

Nagmani, R. and J. M. Bonga, 1985 Embryogenesis in Subcultured Callus of *Larix decidua, Canadian Journal of Forest Research* 15: 1088–1091.

Nagmani, R. and M. R. Becwar 1988 Factors Affecting Somatic Embryo Development in Loblolly Pine. *Abstracts*, 4th International Conifer Tissue Culture Work Group, Aug. 8–12, 1988, Saskatoon Saskatchewan, Canada.

Singh, Hadev 1978 "Embryo", in *Embryology of Gymnosperms*, Chapter 11, Gebruder Borntrager, Berlin.

Tautorus, T. E., S. M. Attree, L. C. Fowke, and D. I. Dunstan 1990 Somatic Embryogenesis from Immature Zygotic Embryos, and Embryo Regeneration from Protoplasts in Black Spruce (*Picea Mariana* Mill.), *Plant Science* 67: 115–124.

Teasdale, Robert D., Pamela A. Dawson, and H. W. Woolhouse, 1986 Mineral Nutrient Requirements of a Loblolly Pine. (*Pinus Taeda* Cell Suspension Culture. *Plant Physiology* 82:942–945.

Gurpta et al. (1987) Biotechnolog vol. 5, pp. 710–712.

Gupta et al. (1987) Biotechnology vol. 5, pp. 147–151.

Gupta et al. (1986) Biotechnology vol. 4, pp. 643–645.

HIGH CONCENTRATION ENRICHMENT OF CONIFER EMBRYONAL CELLS

This application is a continuation-in-part of our earlier application Ser. No. 321,035, filed Mar. 9, 1989.

BACKGROUND OF THE INVENTION

The present invention relates to the method for reproducing coniferous plants by somatic embryogenesis using the techniques of plant tissue culture. It is especially directed to production of totipotent embryonal cells in high concentrations relative to associated nonembryogenic cells. These cells are particularly useful for processes involving genetic manipulation and high frequency recovery of genetically transformed plantlets.

Loblolly pine (*Pinus taeda* L.), its closely related southern pines, and Douglas-fir (*Pseudotsuga menziesii* (Mirb.) Franco) are probably the most important commercial species of temperate North American timber tress. Similarly, Norway spruce (*Picea abies* (L.) Karst.) is probably the most important European softwood species. Since the early 1940s, when serious private reforestation efforts began, literally billions of one and two year old nursery-grown trees have been planted worldwide on cut-over or burned forest lands. For many years these seedling trees were grown using naturally produced seed from cones collected as a part time effort of individuals seeking to supplement their incomes. As early as 1957 forest geneticists began to plant seed orchards using either seed or grafted scions obtained from superior trees. These trees were selected for such inheritable characteristics as rapid growth, straightness of bole, wood density, etc. Now in both the southern pine and Douglas-fir regions the bulk of the seed is produced from selected trees grown in seed orchards, some of them now second and third generation orchards.

Despite the fact that the orchards were stocked with superior trees, pollination often cannot be carefully controlled and frequently the seed trees are fertilized by wild pollen of unknown characteristics. For this reason, the characteristics of the progeny produced by sexual reproduction have not been as predictable as hoped and genetic gain could not be attained as rapidly as desired.

Beginning about 1960, techniques were developed for reproducing some species of plants by tissue culture. These were predominately angiosperms and usually ornamental house plants. The method employed use of a suitable explant or donor tissue from a desirable plant. This was placed on a series of culture media in which nutrients and growth hormones were carefully controlled from step to step. The usual progression was growth from the explant to a callus. The callus was placed on a budding medium where adventitious buds formed. These, in turn, were separated, elongated, and rooted to ultimately form plantlets. A plantlet has the nature of a seedling but is genetically identical to the explant donor plant.

Gymnosperms in general, and most forest tree species in particular, proved to be much more difficult to reproduce by tissue culture. It was not until about 1975 that Douglas-fir was successfully reproduced by organogenesis. Loblolly pine was successfully reproduced about two years later.

Culture by organogenesis is tedious and expensive due to the large amount of delicate manual handling necessary. It was soon recognized that embryogenesis was potentially a much more desirable method from the standpoints of quantity of plantlets produced, cost, and potential genetic gain. Work on embryogenesis of forest species began in the late 1970s. U.S. Pat. No. 4,217,730 to El-Nil describes one early attempt at somatic embryogenesis of Douglas-fir. This approach was later set aside because advanced stage embryos and plantlets could not be readily obtained. However, other workers entered the field in increasing numbers and progress has been rapid even if it has not until the present time reached the commercial stage. A brief review of some of the most important work will follow. This is intended to be representative and is not fully inclusive of all the work in the field. Literature citations in the text are given in abbreviated form. Reference should be made to the bibliography at the end of the specification for full citations of the literature noted herein.

The natural embryogeny of gymnosperms is described in great detail by Singh (1978). Conifer-type embryogeny is one of four types noted for gymnosperms. This includes virtually all of the important forest species except *Sequoia*. Singh notes that the immature seeds typically contain more than one embryo. Most commonly this seems to occur when a single zygote forms multiple embryos, a phenomenon called "cleavage polyembryony". As the seed matures one embryo becomes dominant while the others are suppressed. The ability to form multiple embryos from a single zygote forms the basis for most of the present embryogenic processes for multiplying conifers. However, Douglas-fir is an exception. Most typically only a single embryo will be present throughout the formation and maturation of a seed. This may account for at least some of the difficulty experienced to date in multiplying Douglas-fir by somatic embryogenesis.

Bourgkard and Favre (1988) describe what is the apparently successful production of plantlets by somatic embryogenesis of *Sequoia sempervirens*. As a historic note, this was one of the first forest tree species successfully reproduced by organogenesis.

Hakman and her coworkers have concentrated on Norway spruce (*Picea abies*), apparently with some success. In a paper by Hakman, Fowke, von Arnold, and Eriksson (1985) the authors describe the production of "embryos" but not plantlets. Hakman and von Arnold (1985) do suggest that they have successfully obtained plantlets. This latter paper is interesting for its comments on the variability within the species and the poor success with many of the seed sources used for explants. The authors suggest that this variability may be due to the physiological condition of the source material. However, other workers have noted great differences in behaviour between recognized genotypes of the species.

Nagmani and Bonga (1985) describe embryogenesis from megagametophytes of *Larix decidua* by tissue culture. The archegonia, proembryos, or embryos with their suspensors were removed prior to culture. Some of the resulting embryos produced in culture were stated to have further advanced to become plantlets established in soil. The ploidy of these plants was not investigated.

Successful production of small quantities of plantlets has now been reported for loblolly pine. Teasdale, Dawson, and Woolhouse (1986) showed the criticality of proper mineral nutrients for cell suspension cultures of loblolly pine. The article by Becwar, Wann, and Nagmani (1988) is enlightening for the differences shown in performance between different families (or genotypes). Three families out of the ten tried accounted for most of their success. Even so, they appeared unable to grow cotyledonary embryos. A companion paper by Nagmani and Becwar (1988) showed development of *Pinus taeda* to the precotyledonary stage. In an earlier paper, Gupta and Durzan (1987a) described their success in taking loblolly pine to the plantlet stage by embryogenesis. However, only one genotype was successfully taken to the plantlet stage and only one converted plant was produced. The authors note the need for "improved conversion rates" as well as other information before the process can be considered commercially practical.

Sugar pine (*Pinus lambertiana*) has also been cultured to the plantlet stage as reported by Gupta and Durzan (1986). The authors note a very low 1-2% conversion of embryos into plantlets.

The above researchers appear to be the only ones who have previously reported success in producing Douglas-fir plantlets by somatic embryogenesis (Durzan and Gupta 1987). Again, the success ratio appears to be very low and they have obtained only two converted plants from a single genotype.

In our parent to the present application, Ser. No. 321,035, filed Mar. 9, 1989, now U.S. Pat. No. 4,957,866 herein incorporated by reference, we described an improved method for reproducing coniferous species by somatic embryo-genesis. An intermediate high osmoticant culture medium was used to generate strong late stage proembryos, prior to the development of mature cotyledonary embryos in another medium containing abscisic acid. This step led to a very significantly improved success rate in attaining robust somatic embryos that could be converted into growing plants.

Genetic manipulation has been used on numbers of plant species to introduce naturally lacking characteristics, such as resistance to specific diseases. The use of these techniques is in its infancy, as far as forest tree species are concerned, even though they could prove to be an extremely important part of a tree improvement program.

Removal of cell walls to create protoplasts opens one route to genetic modification. Gene transfer can be accomplished using such techniques as electroporation, protoplast fusion, and DNA uptake. Early work along these lines has not been so much concerned with genetic modification per se as with the development of techniques to obtain viable regenerated cells for further development. A number of examples can be cited. These papers are typical of the work reported to date and are not offered as an exhaustive survey of the literature on conifer protoplasts. Gupta and Durzan (1987b) showed that protoplasts can be formed from very early somatic embryos of loblolly pine. Cell walls were successfully regenerated on these protoplasts and culture was resumed so that somatic embryos were ultimately obtained. Successful conversion to plants was not reported.

Attree and coworkers (1989) report regeneration of white spruce (*Picea glauca* (Moench) Voss) protoplasts which had been isolated from cryopreserved embryogenic tissue. Cotyledonary embryos formed from the regenerated protoplasts were ultimately successfully germinated, although the authors do not indicate whether any of the germinants were ultimately converted to plants growing in soil.

Tautorus, et al. (1990) similarly describe the production and regeneration of protoplasts of black spruce (*Picea mariana* Mill.). These authors did not report what progress they had made in achieving germination of somatic embryos.

The efforts noted above are pioneering from the standpoint that they explore one route to ultimate genetic manipulation of conifers. However, many other routes are available and the general methods that can be employed are well known.

The techniques of somatic embryogenesis just discussed appear to provide a particularly useful tool to use in the genetic modification of conifers. However, one problem was not discussed or perhaps even considered by any of the above workers. This is the matter of obtaining a more suitable germ plasm supply for attempted genetic modification. Many, if not most, of the cells present among those available to the present time lack the potential of ultimately developing into embryos useful for growing plants. In addition to the embryonal cells, there is a large volume of attached and free suspensor cells and other nonembryogenic material that, in effect, serves as a very significant diluent. This greatly reduces the statistical probability of a useful modification occurring in a cell that can later be regenerated and further processed to result in a growing plant.

The present invention is directed to the problem of obtaining the high quantities and concentrations of embryonal cells needed for genetic manipulation, by whatever method is chosen, and the high frequency recovery of genetically transformed plantlets.

SUMMARY OF THE INVENTION

The present invention relates to the method of reproducing selected plants by somatic embryogenesis using tissue culture techniques. More specifically, it is a method of generating large quantities of totipotent embryogenic cells in high concentrations relative to cells lacking embryogenic potential. The resulting embryogenic cells are particularly suitable for genetic manipulation although they may also be used for other purposes as well.

The present method is particularly suitable for ultimately producing genetically modified and improved woody gymnosperms of the order Coniferales. It is especially well suited for generating large clones of superior forest trees for reforestation, including, species within the families Pinaceae, Cupressaceae, and Taxodiaceae. Most or all species within the genera Abies, Pinus, Picea, Tsuga, Pseudotsuga, Thuja, Juniperis, Larix, and Sequoia are believed to be well suited for multiplication by the present method.

The method is particularly advantageous in that it employs standard methods of tissue culture using equipment available in any tissue culture laboratory.

A number of terms are known to have differing meanings when used in the literature. The following definitions are believed to be the ones most generally used in the field of botany and are consistent with the usage of the terms in the present specification.

"Auxins" are plant growth hormones that promote cell division and growth.

"Cytokinins" are plant growth hormones that affect the organization of dividing cells.

"Callus" is generally considered to be a growth of unorganized and either unconnected or loosely connected plant cells generally produced from culturing an explant.

"Embryogenic callus" is a translucent white mucilagenous mass that contains early stage proembryos attached to suspensors. This is also referred to as an "embryonal-suspensor mass" or "ESM" by some investigators.

An "embryonal cell" is one that has the full potential to develop into a somatic embryo and, ultimately, into a plant. Embryonal cells will have large nuclei and dense cytoplasm.

"Embryogenic" refers to cells with the inherent capability of becoming embryonal cells.

A "proembryo" is a cell or group of cells having the potential to become a plant but lacking defined meristematic organ primordia.

An "early stage proembryo" is a mass generally of 1-10 cells with dense cytoplasm and large nuclei that have the potential of forming a plant. The early stage proembryo is normally found as a head associated at the end of a long thin-walled suspensor cell (FIG. 1).

A "late stage proembryo" is a proembryo with a smooth embryonal head of at least about 100 cells associated with multiple suspensor cells. The late stage proembryo is a very robust advanced proembryo (FIG. 2).

A "cotyledonary embryo", sometimes simply referred to as an "embryo", has a well defined elongated bipolar structure with latent meristem with cotyledonary primordia at one end and a potential radicle at the opposite end. The cotyledonary structure frequently appears as a small "crown" at one end of the embryo (FIGS. 3 and 9). A cotyledonary somatic embryo is analogous to a developed zygotic embryo.

An "explant" is a piece of tissue taken from a donor plant for culturing.

A "meristem" or "meristematic center" is a group of tissue forming cells capable of further development into plant organs; e.g., shoots and roots.

An "osmoticant" or "osmoticum" is a chemical material used for controlling the osmotic potential of a solution. In the present context the solution would be a culture medium.

A "plantlet" is a plant asexually reproduced by tissue culture (FIG. 4).

A "converted embryo" is an embryo that has germinated and been established as a plant growing in soil.

"Somatic embryogenesis" is the process using tissue culture techniques for generating multiple embryos from an explant. The embryos from a given tissue source are presumed to be genetically identical.

"Totipotent" means that a cell or group of cells possesses all of the genetic and structural potential necessary to ultimately become a normal plant.

The present method comprises a multistage culturing process. A suitable explant is first placed on an induction or initiation culture medium. This usually will contain relatively high quantities of growth hormones including at least one auxin and frequently one or more cytokinins. However, growth hormones at this initial stage are not always necessary or desirable for induction of early stage proembryos. A number of sources of explants may ultimately prove to be satisfactory for culturing. These include, but are not limited to, tissue from cotyledons, hypocotyls, epicotyls, buds, meristematic centers for buds or roots, and seed embryos. Zygotic embryos removed from seeds are presently preferred. In particular, for species which in the past have proved to be very difficult or impossible to propagate by somatic embryogenesis, the embryos from immature seeds may be preferred. The first stage or induction medium will normally be one of those well known from past work which contain a balanced concentration of inorganic salts and organic nutrient materials, with plant growth hormones included as noted above. Auxins are normally present in concentrations which may initially be as high as about 600 $\mu$M/L, more typically not exceeding about 500 $\mu$M/L. Cytokinins, if present, may initially be as high as 500 $\mu$M/L. The plant growth hormones may include at least one auxin and one cytokinin in a combined initial concentration not exceeding about 1100 $\mu$M/L, more typically not exceeding about 900 $\mu$M/L. The particular auxins and cytokinins used and their exact concentrations, or whether they are used at all, will depend somewhat on the species being cultured and even on the particular genotype within that species. This is something that cannot be easily predicted but can be readily determined experimentally. The induction medium may include activated charcoal or a similar adsorbent for control of the levels of both exogenous and endogenous hormones. Where charcoal is not present the levels of growth hormones would normally be much lower than those just noted.

Culturing during this stage is preferably carried out in the dark, although it may also be carried out under very low light conditions, or in full light until an embryogenic mass forms. Lighting conditions will depend in large part on the composition of the particular medium selected. This embryogenic mass has been described by various other names by researchers who have reported it in the past; e.g., embryogenic callus (Hakman and von Arnold 1985) or embryonalsuspensor mass (Durzan and Gupta 1987). The present inventors will use this latter terminology with the understanding that other investigators may designate it differently. It has the appearance of a whitish, translucent, mucilagenous mass containing early stage proembryos which are readily apparent by low power light microscopy.

Early stage proembryos from the first culture may be directly transferred to a late proembryo development culture medium having significantly reduced plant growth hormones and, for some species, a higher concentration of osmoticants. However, they are preferably first subcultured in a maintenance medium of similar or slightly higher osmotic potential than the induction medium for further multiplication. This multiplication medium will also usually have the concentration of plant hormones significantly reduced below that of the induction medium. By "significantly reduced" is meant lowered by a factor which may typically be one whole order of magnitude. No hormone adsorbent such as activated charcoal is usually necessary or desirable at this time.

The composition of the late proembryo development culture medium differs from the induction medium by having a similar level of plant growth hormones to those present in the maintenance and multiplication medium. However, for many species such as *Pinus taeda* and *Pseudotsuga menziesii*, the late proembryo development media should have a concentration of osmoticants that is significantly raised above that of the induction or multiplication media. The optimum osmoticant levels at each stage will usually differ for each species and often for individual genotypes within a species. For loblolly pine the osmotic level should typically be of the magnitude of at least 200 mM/kg and preferably about 220 mM/kg or even higher. However, lower levels of about 170 mM/kg minimum will suffice for most genotypes of Douglas-fir. The key advantage of this osmotic "pulse" is that proembryo quality and/or size can be significantly improved. Some species such as *Picea abies*, which are relatively easy to reproduce, may not generally require this raised osmotic level, or it may only be necessary for some genotypes. In these cases late proembryo development may usually be achieved without a change in medium composition from the maintenance and multiplication medium.

Incubation at this stage is usually carried out in the dark or in greatly reduced light until robust late stage proembryos have formed. It is at this point that the process, after late stage proembryos have formed, that the process of the present invention is brought into use. Late stage proembryos will have a smooth head with at least 100 cells along with a mass of suspensor cells. The suspensor cells are elongated and highly vacuolated with thin walls and small embryos. In most cases suspensor cells are not embryogenic; i.e., they are not totipotent and are not responsive to environmental changes that would cause them to form proembryos. Suspensor cells occupy a large part of the volume of the drained cells from a suspension culture.

If the late stage proembryos are placed in a medium of similar composition to the late stage development medium, but with the osmotic level raised even higher, they will begin to bud totipotent embryonal cells out of the surface of the head. The osmotic level should be at least 30%, preferably about 50% higher than that of the late stage development medium. After from three to six subcultures these embryonal cells will slough off and be present as individual cells or as small clusters of cells. An important feature of this treatment is that suspensor cell development will be severely inhibited or may be entirely lacking. Thus, the resulting cells may be concentrated and enriched in the sense that the ratio of embryogenic cells to nonembryogenic cells is very significantly increased. Stated in terms of volumetric ratio of drained cells, the embryogenic cell component may be increase by as much as a factor ot ten.

The cells produced by the present process are particularly well suited for use in any of the standard methods of genetic manipulation. Because of their much higher concentration relative to nonembryogenic cells the statistical chances of a beneficial genetic modification occurring and being recovered is greatly increased.

Following the genetic manipulation treatment, of whatever type, the cells are again placed onto an initiation medium to create a new embryonal-suspensor mass. The steps outlined above are repeated up to the point prior to where the late stage proembryos were placed in the high osmotic level cell enrichment medium.

In a conventional tissue culture progression the late stage proembryos would be transferred to a cotyledonary embryo development medium which preferably lacks auxins and cytokinins entirely. Abscisic acid is a new hormone necessary in the development medium. This is preferably used along with activated charcoal so that the effective concentration of abscisic acid is slowly decreased over time.

Following embryo development the embryos may be placed directly on a germination medium for conversion into plantlets. Alternatively, they may be converted into artificial seeds by any of a number of published processes.

The germination medium has no hormones, a lowered organic nitrogen content, and a reduced level of osmoticants. After a sufficient time in darkness followed by light, or a 16 hour light and 8 hour dark photoperiod, the cotyledonary embryos will have developed into plantlets. The time period for germination will be about 1-2 months. The resulting plantlets will have a well developed radicle and cotyledonary structure with a growing epicotyl and are ready for planting in soil.

It is an object of the present invention to produce coniferous plantlets by somatic embryogenesis.

It is another object to produce large quantities of embryonal cells in high concentrations.

It is a further object to provide a supply of embryonal cells that predominate over accompanying cells lacking embryogenic potential.

It is yet another object to provide embryonal cells that can effectively be genetically manipulated to provide new and improved varieties of coniferous trees.

It is also an object to provide a method of generating embryonal cells that may be genetically manipulated with high frequency recovery of genetically transformed plantlets.

These and many other objects will become readily apparent to those skilled in the art by reading the following detailed description, taken in conjunction with the drawings.

DETAILED DESCRIPTION OF THE PREFERRED EMBODIMENTS

Figure 1:
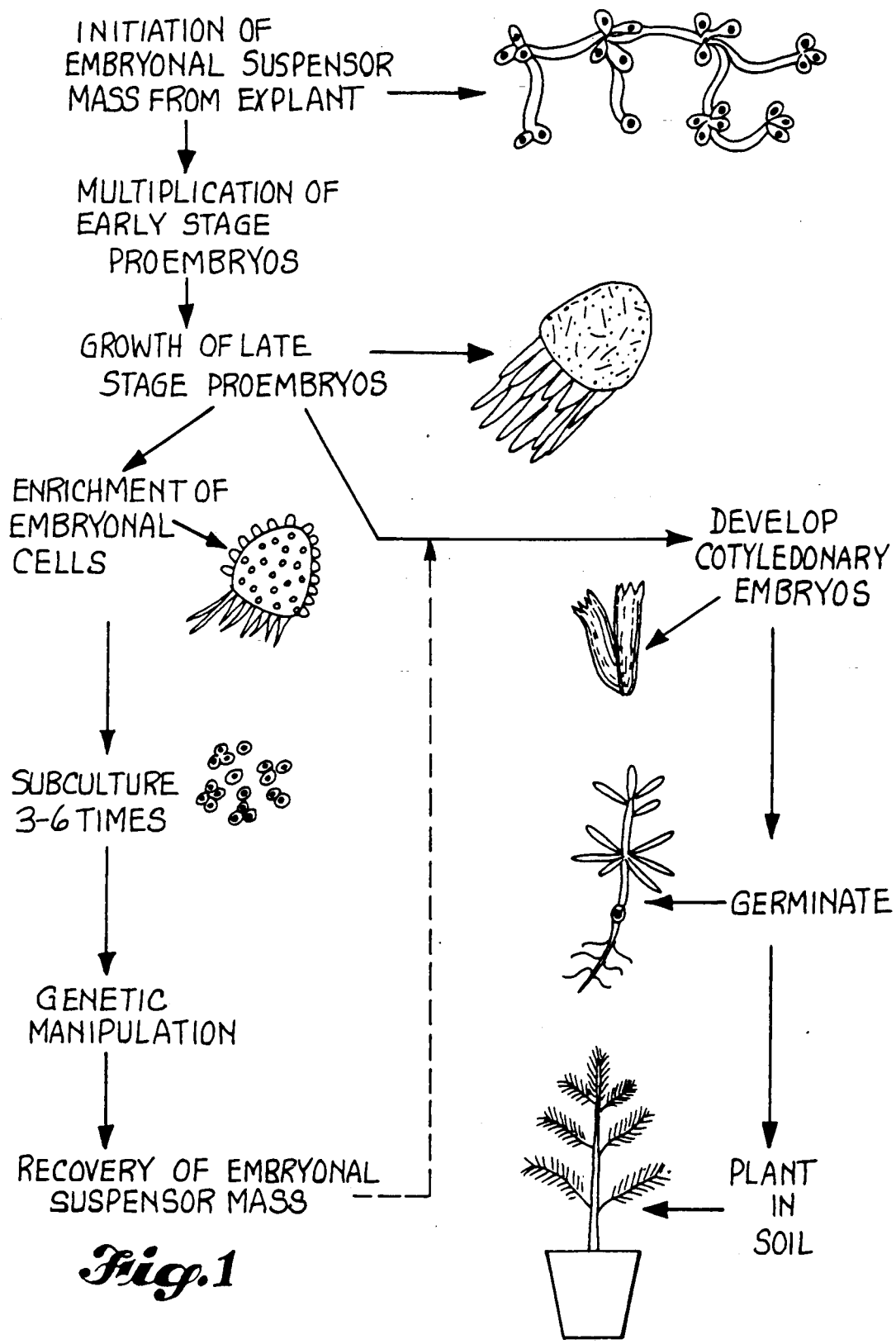
FIG. 1 shows a general outline of the steps in the present method.

Initiation of the process of the present invention is not limited to any single culture medium or to the use of specific growth hormones. Any of a number of well known media, such as that of Murashige and Skoog (1962), may be used. However, the present inventors have found the basal media described in Table 1 to give excellent results. Preferred formulations are given for loblolly pine (*Pinus taeda*), Norway spruce (*Picea abies*), and Douglas-fir (*Pseudotsuga menziesii*). The basal media modified for each of the various culturing stages are given in Table 2.

TABLE 1

| | Basal Culture Media for Three Species | | | |
| | | Concentration, mg/L | | |
| Constituent | LP | NS-I | NS-M | DF |
| SALTS | | | | |
| $NH_4NO_3$ | 603.8 | — | 206.3 | — |
| $KNO_3$ | 909.9 | 50.0 | 2340.0 | 1250.0 |
| KCl | — | 372.5 | — | — |
| $KH_2PO_4$ | 136.1 | 85.0 | 85.0 | 340.0 |
| $Ca(NO_3)_2 \cdot 4H_2O$ | 236.2 | — | — | — |

TABLE 1-continued

Basal Culture Media for Three Species

| Constituent | Concentration, mg/L | | | |
|---|---|---|---|---|
| | LP | NS-I | NS-M | DF |
| CaCl$_2$.6H$_2$O | — | 220.0 | 220.0 | 200.0 |
| MgSO$_4$.7H$_2$O | 246.5 | 160.0 | 185.0 | 400.0 |
| Mg(NO$_3$)$_2$.6H$_2$O | 256.5 | — | — | — |
| MgCl$_2$.6H$_2$O | 50.0 | — | — | — |
| KI | 4.15 | 0.415 | 0.415 | 1.00 |
| H$_3$BO$_3$ | 15.5 | 3.10 | 3.10 | 5.00 |
| MnSO4.H$_2$O | 10.5 | 8.45 | 8.45 | 20.8 |
| ZnSO$_4$.7H$_2$O | 14.4 | 4.30 | 4.30 | 8.0 |
| NaMoO$_4$.2H$_2$O | 0.125 | 0.125 | 0.125 | 0.20 |
| CuSO$_4$.5H$_2$O | 0.125 | 0.0125 | 0.0125 | 0.024 |
| CoCl$_2$.6H$_2$O | 0.125 | 0.0125 | 0.0125 | 0.025 |
| AlCl$_3$ | — | — | — | 0.02 |
| FeSO$_4$.7H$_2$O | 6.95 | 13.90 | 13.90 | 27.85 |
| Na$_2$EDTA | 9.33 | 18.65 | 18.65 | 37.25 |
| ORGANIC ADDITIVES | | | | |
| Sucrose | 30,000.0 | 10,000.0 | 30,000.0 | 15,000.0 |
| myo-Inositol | 1,000.0 | 50.0 | 1,000.0 | 1,000.0 |
| Casamino acids | 500.0 | — | 500.0 | 500.0 |
| L-Glutamine | 1,000.0 | 750.0 | 450.0 | 450.0 |
| Thiamine.HCl | 1.00 | 0.05 | 1.00 | 1.00 |
| Pyridoxine.HCl | 0.50 | 0.05 | 0.50 | 0.50 |
| Nicotinic acid | 0.50 | 0.25 | 0.50 | 0.50 |
| Glycine | 2.00 | — | 2.00 | 2.00 |
| L-Asparagine | — | 50.0 | — | — |

LP-loblolly pine; NS-I-Norway spruce initiation; NS-M-Norway spruce maintenance; DF-Douglas-fir.

TABLE 2

Composition of Media for Different Stage Treatments

LOBLOLLY PINE
ESM Induction - LP + 50 μM 2,4-D + 20 μM KIN + 20 μ BAP + 6,000 mg/L agar.
Early Proembryo Maintenance - LP + 5 μM 2,4-D + 2 μM KIN + 2 μM BAP + 6,000 mg/L agar.
Late Proembryo Development - Early Proembryo Maintenance + 9000 mg/L myo-inositol.
Embryonic Cell Enrichment - Early Proembryo Maintenance + 15,000 mg/L total myo-inositol.
NORWAY SPRUCE
ESM Induction - NS-I + 10.8 μM NAA + 4.4 μM BAP + 7,000 mg/L agar.
Early Proembryo Maintenance - NS-M + 5 μM 2,4-D + 2 μM BAP + 2 μM KIN + 6,000 mg/L agar.
Late Proembryo Development - Same as Early Proembryo Maintenance (may be a liquid medium without agar).
Embryonic Cell Enrichment - Early Proembryo Maintenance without agar and with 10,000 mg/L total myo-inositol.
DOUGLAS-FIR
ESM Induction - DF + 500 μM 2,4-D + 200 μM BAP + 200 μM KIN + 2500 mg/L activated charcoal + 5,000 mg/L agar.
Early Proembryo Maintenance - DF with KNO$_3$ variable between 1250 and 2500 mg/L[1] and sucrose raised to 30,000 mg/L) + 5 μM 2,4-D + 1 μM KIN + 1 μM BAP + 5,000 mg/L agar.
Late Proembryo Development - DF with myo-inositol variable between 1,000-20,000 mg/L[1], L-glutamine raised to 1,000 mg/L, and sucrose raised to 20,000 mg/L + 5 μM 2,4-D + 1 μM KIN + 1 μM BAP.
Embryonic Cell Enrichment - Early Proembryo Maintenance without agar and 1250 mg/L KNO$_3$ with 15,000 mg/L total myo-inositol.
.LH12

[1]Concentration adjusted according to needs of individual genotypes.

A number of abbreviations were used in Table 2 and will also be used in the following text. These are in common use in the field of tissue culture.

BAP—N$^6$-benzylaminopurine (or N$^6$-benzyladenine), a cytokinin

KIN—kinetin (6-furfurylaminopurine), also a cytokinin 2,4-D—2,4-dichlorophenoxyacetic acid, an auxin.

NAA—2-Naphthylacetic acid (Naphthalene-2-acetic acid)

ABA—Abscisic acid

It will be understood by those skilled in the art that other plant growth hormones can be substituted for those just noted. As examples, IAA (indole-3-acetic acid), IBA (indole-3-butyric acid), and NAA (naphthalene-2-acetic acid) are effective auxins and 2-IP (N$^6$-isopentenylaminopurine) and zeatin are frequently used as cytokinins.

As an aid in comparing the present work with other published data, the following table of conversions from weight to molar concentrations might be useful.

| | 1 μM/L | 1 mg/L |
|---|---|---|
| BAP | 0.225 mg/L | 4.44 μM/L |
| KIN | 0.215 | 4.65 |
| 2,4-D | 0.221 | 4.52 |
| NAA | 0.816 | 5.38 |
| ABA | 0.264 | 3.78 |

As knowledge of tissue culture techniques expands, the criticality of osmotic potential control of the media used in the various culturing stages becomes more and more evident. A large group of chemical materials are suitable as osmoticants. In general these are highly water soluble polyhydroxylated molecules that include either simple or complex sugars, hexitols, and cyclitols. The cyclitols are normally six carbon ring compounds that are hexahydroxylated. The most readily available cyclitol is myo-inositol but any of the other eight stereoisomeric forms, such as scyllo-inositol are believed to be quite suitable. Among the sugars, sucrose and glucose are known to be very effective but many others should prove to be equally useful. Sorbitol (D-glucitol), D-mannitol, and galactitol (dulcitol) are straight chain sugar alcohols suitable as osmoticants. Lactose is another sugar effective as an osmoticant. Other materials suitable as osmoticants include glycol ethers such as poly(ethylene glycol) and poly(propylene glycol) and may also include their respective monomers. In the earlier stages of culture; e.g., through late proembryo development, myo-inositol is a preferred osmoticant, normally in admixture with sucrose which provides the main energy source. Myo-inositol is also a preferred osmoticant for the embryonic cell enrichment process of the present invention.

Osmotic levels of the various media through late proembryo development and embryonal cell enrichment are summarized in the following table. It should be noted that these are subject to some adjustment depending on the needs and performance of individual genotypes within each of the species listed.

TABLE 3

Osmolality of Media at Different Stages, mM/kg

| Stage | Species | | |
|---|---|---|---|
| | LP | NS | DF |
| ESM Induction | 155 | 100 | 110 |
| Early Stage Maintenance | 155 | 155 | 155 |
| Late Stage Proembryo Devel. | 220 | 155 | 165–240 |
| Embryonic Cell Enrichment | 300 | 240 | 300–360 |
| Cell Wall Regeneration | 610 | 590 | 620 |

In the following example one species, loblolly pine, will be followed through the process from initiation through germination and conversion to growing trees. It will be understood that similar treatments will apply to other species. Preferred media for the various treatment steps up to the time of embryonic cell enrichment are also given in Tables 1 and 2 for Norway spruce and Douglas-fir.

Reference to FIG. 1 at this time will provide an overall outline of the treatments to be described.

EXAMPLE 1

The following schedule of treatments has been very successfully used for the growth and conversion of plantlets by somatic embryogenesis of loblolly pine (*Pinus taeda*). Explants were immature embryos dissected from seeds 4 to 5 weeks after fertilization. Seeds were obtained from cones supplied by a Weyerhaeuser Company seed orchard located at Washington, N. C. The cones were stored at 4° C. until used. Immediately before removal of the immature embryos the seeds were sterilized using a modified method of Gupta and Durzan (1985). Briefly, this involves an initial washing and detergent treatment followed by a first sterilization in 30% $H_2O_2$ and a second in diluted 10% v/v household bleach. The additional $HgCl_2$ treatment used by Gupta and Durzan was not found to be necessary to ensure sterility. The explants were thoroughly rinsed with sterile distilled water after each treatment.

Stage I—Induction

Sterile dissected embryos were placed on a solid embryonal-suspensor mass (ESM) induction medium and held in an environment at 22°-25° C. with a 24 hour dark photoperiod for a time of 3-5 weeks. The length of time depended on the particular genotype being cultured. At the end of this time a white mucilagenous mass had formed in association with the original explants. This appears to be identical with that described by Gupta and Durzan (1987). Microscopic examination revealed numerous early stage proembryos associated with the mass. These are generally characterized as having a long thin-walled suspensor associated with a small head generally having less than 10 individual cells, each with dense cytoplasm and large nuclei. Early stage proembryos are illustrated in FIG. 1. The osmolality of the medium was 158 mM/kg.

Stage II—Maintenance and Multiplication

Early stage proembryos from the ESM generated in the induction stage were placed on a maintenance medium. This differs from the induction medium in that the growth hormones (both auxins and cytokinins) were reduced by a full order of magnitude. The temperature and photoperiod were again 22°-25° C. with 24 hours in the dark. Osmolality of this medium will typically be similar or identical to that of the induction medium. In the present example it was identical. Proembryos developed in this stage were similar in appearance to those from Stage I and were subcultured every 12-15 days.

Stage III—Late Stage Proembryo Development

Figure 3:
FIG. 3 is a photomicrograph of a late stage proembryo.

Early stage proembryos from either Stage I or Stage II, preferably the latter, were placed on a solid late proembryo development medium. This medium has the same growth hormone concentration as the maintenance medium. However, the osmoticant was raised to a much higher concentration. In this case the osmoticant, myo-inositol, was at a concentration of 10,000 mg/L or 1% on a w/v basis. Osmotic potential was measured as 240 mM/kg. Temperature and photoperiod were the same as for Stages I and II. After 3 or 4 subcultures of about 12-15 days each, very robust late stage proembryos had formed. These are characterized by smooth embryonal heads generally having in the neighborhood of over 100 individual cells with multiple suspensors, as exemplified in FIG. 3.

Osmotic potential of the late proembryo development medium should most typically be in the neighborhood of about 30-50% higher than that of the induction or multiplication media. As was noted earlier, the requirements for elevation of osmotic potential at this stage will vary for different species and for different genotypes within the same species.

Alternatively, the Stage II and/or Stage III proembryos could be cultured for late proembryo development in suspension in a liquid medium of similar composition to the above but lacking the agar. In this case subcultures should be made every 7-8 days.

It is preferred that early stage proembryos brought into Stage III culture should have a Stage II subculturing for rapid multiplication of the particular clone. However, on occasions where time may be of greater importance than quantity, early stage proembryos from Stage I may be taken directly into Stage III.

Stage III-A—Embryonic Cell Enrichment

Figure 4:
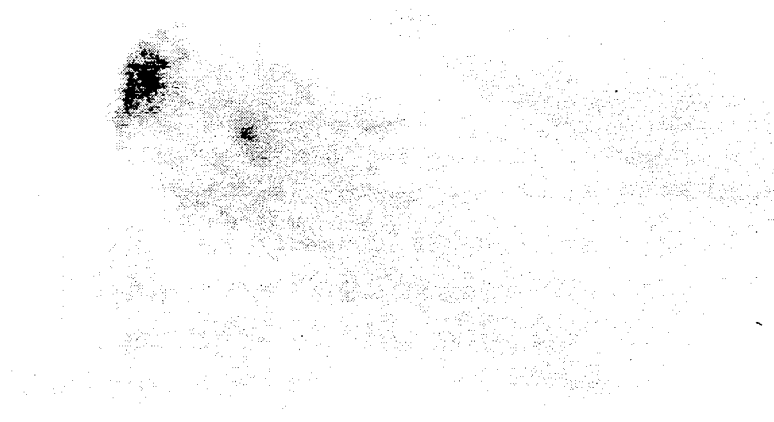
FIGS. 4 and 5 are photomicrographs of proembryos generating large quantities of embryonal cells.
Figure 5:
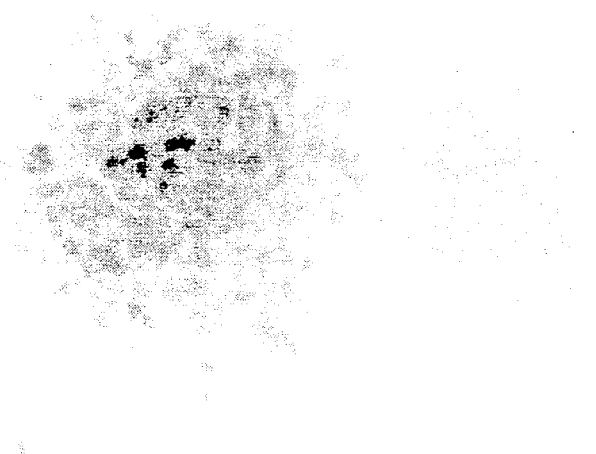

In a usual tissue culture sequence the late stage proembryos would now be placed in or on a development medium lacking auxins and cytokinins but having abscisic acid for the growth of cotyledonary embryos. However, using the method of the present invention, when a high concentration of embryonal cells is desired the late stage proembryos are placed instead on a liquid or solid medium of similar composition to the previous one except for the osmotic level. This is raised by 30-80% over that of the late stage proembryo development medium. Preferably the osmotic level increase will be in the 35-55% range. Myo-inositol is a preferred osmoticant. For loblolly pine a preferred usage is 15,000 mg/L or 1.5% on a w/v basis. The resulting medium has an osmotic level of about 300 mM/kg. Subcultures are made every 12-15 days if solid a medium is used and weekly if the medium is a liquid type. After one or two subcultures the formerly smooth late stage proembryos (FIG. 3) take on what is best described as a "fuzzy" appearance with reduced prominence of suspensor cells (FIG. 4). This is due to the budding from the head of many embryonal cells. After from three to six subcultures the heads will have an appearance similar to those shown in FIG. 5 where suspensor cells are essentially absent. Now the embryonal cells will begin to slough off as single cells or small clusters of cells. For some genotypes additional subculturing may be necessary. These embryonic cells appear identical to early stage proembryos except that they either lack suspensors entirely or the suspensors are greatly suppressed. This is of great importance if genetic manipulation is contemplated. Suspensors are not embryogenic and occupy a large portion of the tissue volume in a drained or otherwise concentrated culture.

The aggregate of cells and cell clumps is particularly useful for genetic manipulation by any of the established routes. As is discussed by Gupta and Durzan (1987b), cell walls may be enzymatically removed to create protoplasts. This paper is herein incorporated by reference. The protoplasts can be treated by means such as electroporation to introduce specific desirable genes. After such treatment, the cell walls are regenerated in a very high osmotic level medium, with an osmolality of about 600 mM/kg. For the three species specifically described herein the regeneration medium will normally be a standard early proembryo maintenance medium with total myo-inositol raised to 40,000 mg/L along with 10,000 mg/L glucose and 5,000 mg/L sorbitol as additional components. From this point they may be returned to an early stage maintenance medium for normal development of new embryonal-suspensor masses and early stage proembryos. Alternatively, they may be maintained, essentially in singulated form, on the high osmotic level regeneration medium where they remain as embryonal masses without significant development of suspensors. In this latter condition they are readily available for additional experimentation.

Stage IV—Cotyledonary Embryo Development

Late Stage III proembryos are transferred to a solid or liquid medium that either lacks growth hormones entirely or has them present only at very low levels. This has the same lower level of osmoticants as Stages I and II. However, abscisic acid (5-(1-hydroxy-2,6,6-trimethyl-4-oxo-2-cyclohexen-1-yl)-3-methyl-2,4-pentadienoic acid) is included as a necessary material for further development. It is beneficial if an adsorbent material is also present in this medium. The adsorbent may be chosen from a number of chemical materials having extremely high surface area and/or controlled pore size such as activated charcoal, soluble and insoluble forms of poly(vinyl pyrrolidone), activated alumina, silica gel, molecular sieves, etc. The adsorbent will normally be present in a concentration of about 0.1-5 g/L, more generally about 0.25-2.5 g/L. The contribution of the adsorbent is not fully understood. However, it is known to cause a gradual drop in the level of available abscisic acid during the development period.

The osmotic potential of this medium will generally be about 170 mM/kg for loblolly pine. However, for some species, particularly Douglas-fir but others as well, a much higher osmolality is beneficial. As before, development was carried out in complete darkness at a temperature of 22°-25° C. Development time was 4-6 weeks after which cotyledonary embryos 4-5 mm long were present. These had a very similar appearance to fully mature zygotic embryos.

Stage V—Germination

Cotyledonary embryos from the development stage were placed on a solid medium for germination. This is a basal medium lacking growth hormones which has been modified by reducing sucrose to 20,000 mg/L, myo-inositol to 100 mg/L, L-glutamine to 200 mg/L, and entirely omitting casamino acids. After about 6-8 weeks under environmental conditions of 23°-25° C. and a 16 hour light/8 hour dark photoperiod the resulting plantlets were approximately 20 mm in length and had a well developed radicle and hypocotyl and green cotyledonary structure and epicotyl. The young plantlets are illustrated in FIG. 1.

Because of the reduced carbohydrate concentration, the osmotic potential of the germination medium is further lowered below that of the development medium. It will normally be below about 150 mM/kg and was, in the present example, about 100 mM/kg.

Stage VI—Plant Growth

Plantlets from Stage V are removed from the culture medium and planted in a soil comprising equal parts of peat and fine perlite. At this point they begin to develop in a manner similar to conventional seedlings.

EXAMPLE 2

A similar tissue culture routine to that described above was carried out using Norway spruce. As with loblolly pine, the explants were zygotic embryos but in this case they were dissected from mature seeds. Culture media used are described in Tables 1 and 2. Following the cell concentration and enrichment step, two day old cultures were used for the isolation of protoplasts using the techniques of Gupta and Durzan (1987b). High frequency cell colonies were obtained when protoplasts were embedded in a thin layer of agarose and placed on filter paper over a feeder layer of actively growing Norway spruce embryonal-suspensor masses. Typical conifer-type polymebryogenesis was observed during protoplast regeneration. Suspension cultures were then established in a maintenance medium from the resulting embryonal-suspensor masses. Up to thirty mature cotyledonary somatic embryos were ultimately obtained per mL of culture when placed on a development medium containing abscisic acid. Over 70 complete plantlets have been regenerated within about six months from the protoplasts and are now established in soil for field testing.

EXAMPLE 3

In similar fashion to the work reported in the previous examples for loblolly pine and Norway spruce, several genotypes of Douglas-fir were cultured through embryonal cell enrichment Stage III-A, using the media of Tables 1 and 2. After several subcultures on a maintenance medium with either 10,000 or 15,000 mg/L myo-inositol, large quantities of embryonal cells without suspensors were observed to have formed on all genotypes. At a myo-inositol concentration of 10,000 mg/L only the "fuzzy head" stage was reached. The higher concentration is necessary before the cells begin to slough off as individual cells or small clumps of cells lacking suspensors.

While inorganic salts and pure simple organic chemicals generally behave similarly in culture media regardless of supplier, there are occasions when this is not the case for the more complex materials. Without intending endorsement of any product over available alternatives, chemicals from the following suppliers were used throughout the experiments described in the example. Agar was obtained from Difco Laboratories, Detroit Mich. Protoplasts were regenerated by first solidifying them in drops of SeaPlaque agarose from FMC Bioproducts, Rockland, Me., prior to placing the resulting wafers in the regeneration medium. Casamino acids, a casein hydrolysate, was also supplied by Difco Laboratories. Activated charcoal was obtained from Sigma Chemical Company, St. Louis, Miss., as their grade NuC-4386.

Figure 2:
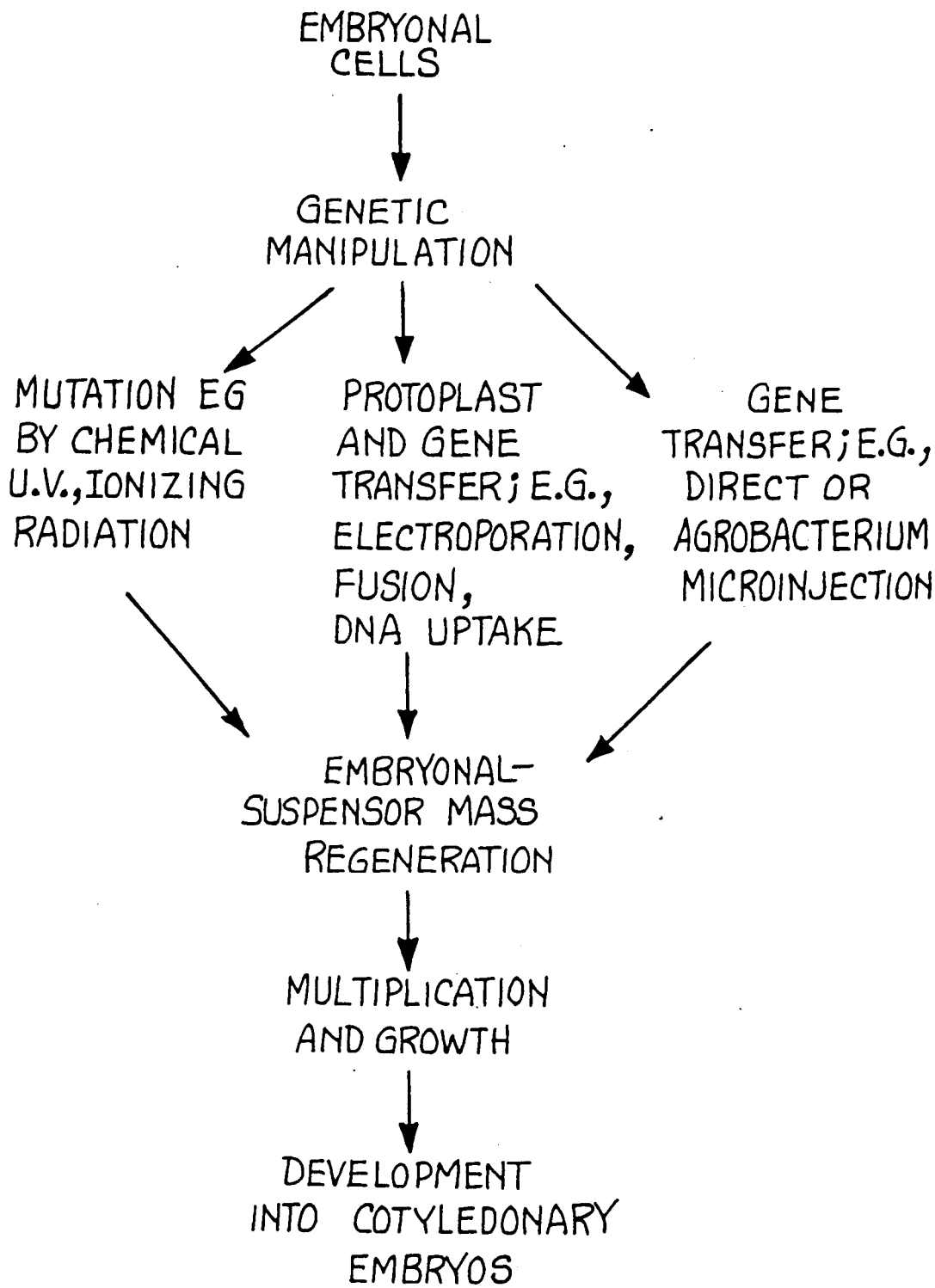
FIG. 2 shows an outline of ways in which embryogenic cells may be genetically modified.

FIG. 2 shows in outline form some of the various routes to genetic modification for which the Stage III-A embryonal cells can be advantageously employed. As one route they can be treated directly with chemicals, such as nitrogen mustards, which are known mutagens. In similar fashion they can be exposed to ultraviolet radiation or ionizing radiation such as X-rays or gamma rays.

The creation and use of protoplasts has already been noted. Protoplasts offer a number of alternative paths to genetic manipulation. These include electroporation in which selected genes are literally shot through a mass of cells susceptible to modification. The known techniques of protoplast fusion and DNA uptake are also useful.

Gene transfer can be accomplished by techniques such as microinjection or the use of an Agrobacterium vectoring agent.

Whatever means of genetic manipulation or other treatment is used, the efficiency of the process will be greatly improved due to the much higher concentration of embryogenic cells relative to competing cells that do not have totipotent capabilities.

There are strong indications that enriched concentrates of embryonal cells can be stored at cryogenic temperatures with much greater success than is the case for embryos derived from an embryonal-suspensor mass with attached suspensor cells.

It will be evident to those skilled in the art that the present invention has usefulness well beyond that which has been discussed or exemplified. These variations should be considered to be within the scope of the invention if encompassed within the limits of the following claims.

BIBLIOGRAPHY

Abo El-Nil, Mostafa
   1980 Embryogenesis of gymnosperm forest trees. U.S. Pat. No. 4,217,730.

Attree, S. M., D. I. Dunstan, and L. C. Fowke
   1989 Plantlet regeneration from embryogenic protoplasts of white spruce (*Picea glauca*). *Bio/Technology* 7: 1060-1062.

Becwar, M. R., S. R. Wann, and R. Nagmani
   1988 A survey of initiation frequency of embryogenic callus among ten families of *Pinus taeda* (loblolly pine). *Abstracts*, 4th International Conifer Tissue Culture Work Group, Aug. 8-12, 1988, Saskatoon, Saskatchewan, Canada.

Bourgkard, F. and J. M. Favre
   1988 Somatic embryos from callus of *Sequoia sempervirens*. *Plant Cell Reports* 7: 445-448.

Durzan, D. J. and P. K. Gupta
   1987 Somatic embryogenesis and polyembryogenesis in Douglas-fir cell suspension cultures. *Plant Science* 52: 229-235.

Gupta, Pramod K. and Don J. Durzan
   1986 Somatic polyembryogenesis from callus of mature sugar pine embryos. *Bio/Technology* 4: 643-645.
   1987a Biotechnology of somatic polyembryogenesis and plantlet regeneration in loblolly pine. *Bio/Technology* 5: 147-151.
   1987b Somatic embryos from protoplasts of loblolly pine proembryonal cells. *Bio/Technology* 5: 710-712.

Hakman, Inger and Sara von Arnold
   1985 Plantlet regeneration through somatic embryogenesis in *Picea abies* (Norway spruce). *Journal of Plant Physiology* 121: 149-158.

Hakman, Inger, Larry C. Fowke, Sara von Arnold, and Tage Eriksson
   1985 The development of somatic embryos in tissue cultures initiated from immature embryos of *Picea abies* (Norway spruce). *Plant Science* 38: 33-35.

Murashige, Toshio and Folke Skoog
   1962 A revised medium for rapid growth and bioassays with tobacco tissue cultures. *Physiologia Plantarum* 15: 473-493.

Nagmani, R. and J. M. Bonga.
   1985 Embryogenesis in subcultured callus of *Larix decidua*. *Canadian Journal of Forest Research* 15: 1088-1091.

Nagmani, R. and M. R. Becwar
   1988 Factors affecting somatic embryo development in loblolly pine. *Abstracts*, 4th International Conifer Tissue Culture Work Group, Aug. 8-12, 1988, Saskatoon Saskatchewan, Canada.

Singh, Hardev
   1978 "Embryo" in *Embryology of Gymnosperms*, Chapter 11, Gebruder Borntrager, Berlin.

Tautorus, T. E., S. M. Attree, L. C. Fowke, and D. I. Dunstan
   1990 Somatic embryogenesis from immature zygotic embryos, and embryo regeneration from protoplasts in black spruce (*Picea mariana* Mill.) *Plant Science* 67: 115-124.

Teasdale, Robert D., Pamela A. Dawson, and Harold W. Woolhouse.
   1986 Mineral nutrient requirements of a loblolly pine. (*Pinus taeda* cell suspension culture. *Plant Physiology* 82: 942-945.

We claim:
1. A method of generating high concentrations of conifer embryonal cells which comprises:
   placing a suitable explant on an initiation culture medium containing sufficient amounts of nutrients and plant growth hormones and growing an embryonal-suspensor mass containing early stage proembryos;
   transferring said early stage proembryos to a second culture medium sufficiently reduced in plant growth hormones in order to multiply said proembryos and develop late stage proembryos;
   transferring the late stage proembryos to a third culture medium with a sufficient amount of plant growth hormones and a sufficiently raised osmotic level to cause formation and enrichment of large quantities of totipotent embryonal cells on the surface of the late stage proembryos;

subculturing the embryonal cells so produced for a sufficient number of times, using a medium of similar composition and osmotic potential to said third culture medium, so that totipotent embryonal cells slough off as individual cells or clusters of cells; and recovering said totipotent embryonal cells.

2. The method of claim 1 in which the osmotic level of the embryonal cell enrichment medium is elevated at least about 30% over the osmotic level of the late stage proembryo development medium.

3. The method of claim 2 in which the osmotic level is raised at least about 35-55% over the level of the late stage proembryo development medium.

4. The method of claim 1 which further comprises removing the walls of the totipotent embryonal cells to create large numbers of embryonal protoplasts suitable for genetic manipulation.

5. In a method of generating conifer embryonal cells by tissue culture by first growing an embryonal suspensor mass containing early stage proembryos on a first culture medium, then further culturing said embryonal-suspensor mass on a second culture medium to develop late stage proembryos, the improvement which comprises;

transferring the late stage proembryos to a third culture medium with a sufficient amount of plant growth hormones and a sufficiently raised osmotic level to cause formation of large quantities of embryonal cells; and subculturing the embryonal cells so produced for a sufficient number of times until totipotent embryonal cells slough off as individual cells or small clusters of cells so as to increase the ratio of embryogenic to nonembryogenic cells.

6. The method of claim 5 in which the osmotic level of the third culture medium is elevated at least about 30% over the osmotic level of the late stage proembryo development medium.

7. The method of claim 6 in which the osmotic level is raised at least about 35-55% over the level of the second medium used for development of late stage proembryos.

8. The method of claim 5 which further comprises removing the cell walls of the totipotent embryonal cells to create large numbers of totipotent embryonal protoplasts suitable for genetic manipulation.

* * * * *